(12) United States Patent
Wilchek et al.

(10) Patent No.: US 6,632,929 B1
(45) Date of Patent: *Oct. 14, 2003

(54) AVIDIN DERIVATIVES AND USES THEREOF

(75) Inventors: Meir Wilchek, Rehovot (IL); Edward A Bayer, Raanana (IL); Heike Hofstetter, DeKalb, IL (US); Margherita Morpurgo, Teolo (IT)

(73) Assignee: Yeda Research and Development Co. LTD (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/831,499

(22) PCT Filed: Nov. 10, 1999

(86) PCT No.: PCT/IL99/00605
§ 371 (c)(1),
(2), (4) Date: Aug. 7, 2001

(87) PCT Pub. No.: WO00/27814
PCT Pub. Date: May 18, 2000

(30) Foreign Application Priority Data

Nov. 10, 1998 (IL) .................................................. 126990

(51) Int. Cl.⁷ ............................ C07K 1/00; C07K 1/13; G01N 33/532; G01N 33/545; G01N 33/552; G01N 33/553; C07D 273/02
(52) U.S. Cl. ..................... 530/409; 435/7.5; 436/526; 436/527; 436/529; 436/531; 540/455
(58) Field of Search ................. 530/408, 409; 435/7.5; 436/526, 527, 531, 529; 540/455

(56) References Cited

U.S. PATENT DOCUMENTS 5,182,203 A 1/1993 Ebersole et al.

FOREIGN PATENT DOCUMENTS

WO WO 97100329 3/1997

OTHER PUBLICATIONS

Morpurgo et al (1998), "A Chemical Approach To Illustrate the Principle of Signal Transduction Cascades Using the Advin—Biotin System", J. Am.Chem.Soc., 120:12734–12739.

Tsurui Hironori,"PEG–Modified Avidin and Method for Separating Antigen or Antibody Using the Same", Patent Abstracts of Japan, Publ. No. 08012699, Publ. Date Jan. 16, 1996; vol. 1996, No. 5, May 31, 1996.

Green, M. "Avidin and Streptavidin", Methods in Enzymology, US, Academic Press Inc., San Diego, CA, vol. 184, Jan. 1, 1990, pp. 51–67.

Primary Examiner—Mary E. Ceperley
(74) Attorney, Agent, or Firm—Browdy and Neimark, P.L.L.C.

(57) ABSTRACT

A covalent conjugate of a 4'-hydroxyazobenzene-2-carboxylic acid derivative (HABA) and an avidin-type molecule, of the formula:

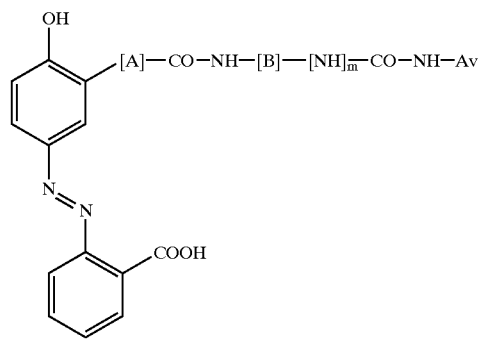

wherein A is $(CH_2)_n$ or $-CH=CH-$, wherein n is an integer from 0–10; B is $(CH_2)_n$ wherein n is an integer from 2 to 10; m is zero or 1; and Av is the residue of an avidin-type molecule selected from the group comprising native egg-white avidin, recombinant avidin, deglycosylated avidins, bacterial streptavidin, recombinant streptavidin, truncated streptavidin and other derivatives of said avidin-type molecules. These HABAylated avidins are red colored in the quinone configuration and can be used in many applications in the avidin-biotin technology.

15 Claims, 4 Drawing Sheets

AVIDIN DERIVATIVES AND USES THEREOF

CROSS-REFERENCE TO RELATED APPLICATIONS

The present application is the national stage under 35 U.S.C. 371 of international application PCT/IL99/00605, filed Nov. 10, 1999 which designated the United States, and which international application was published under PCT Article 21(2) in the English language. The entire contents of said PCT/IL99/00605 are hereby incorporated by reference.

FIELD OF THE INVENTION

The present invention relates to red colored covalent conjugates of 4'-hydroxyazobenzene-2-carboxylic acid derivatives (hereinafter HABA) and an avidin-type molecule, these conjugates referred herein as "HABAylated avidins", and their application in the avidin-biotin technology.

BACKGROUND OF THE INVENTION

Avidin and streptavidin are tetrameric proteins that, due to their strong interaction with biotin, have become widely useful as extremely versatile, general mediators in a broad variety of bioanalytical applications, including chromatography, cytochemistry, cell cytometry, diagnostics, immunoassays and biosensing, gene probes and drug delivery (Wilchek and Bayer, 1990). The reason for their popularity is based on the basic principle of the avidin-biotin technology, namely, that the interaction between avidin and biotin is not affected when biotin is covalently bound to macromolecules or to insoluble carriers (matrices). The biotin moiety can be recognized by the native avidin molecule or derivatized avidin, which contains desired reporter groups.

Avidin (from egg-white) and streptavidin (from *Streptomyces avidinii*) are two related proteins that bind biotin with similar dissociation constants of about $10^{-15}$M. In addition to the binding of biotin, many of their physical properties are quite similar. Both, for example, are constructed of four non-covalently attached identical subunits, each of which bears a single biotin-binding site. The subunit $M_r$ values are also very similar. Moreover, several short stretches in the sequences of the two proteins are preserved, particularly two Trp-Lys stretches that occur at approximately similar positions.

Despite these similarities, several differences exist between the two proteins. Avidin is a disulphide-bridged glycoprotein containing two methionine residues, whereas streptavidin is not glycosylated and is devoid of sulphur-containing amino acid side chains. Another significant difference is in the tyrosine content. Avidin has only one tyrosine residue (Tyr-33), whereas streptavidin has six tyrosine residues at positions 22, 43, 54, 60, 83 and 96. Interestingly, the single tyrosine residue of avidin is located in a region which contains a sequence identical with that of one of the streptavidin tyrosine residues (Tyr-43 in the stretch Thr-Gly-Thr-Tyr).

Each avidin monomer binds one molecule of biotin. The unique feature of this binding, of course, is the strength and specificity of formation of the avidin-biotin complex. The resultant affinity constant, estimated at $1.6 \times 10^{15}$ M$^{-1}$ for avidin and $2.5 \times 10^{13}$ M$^{-1}$ for streptavidin, is the highest known for a protein and an organic ligand. It is so strong that biotin cannot be released from the binding site, even when subjected to a variety of drastic conditions such as high concentrations of denaturing agents at room temperature, e.g., 6 M guanidinium hydrochloride, 3 M guanidinium thiocyanate, 8 M urea, 10% β-mercaptoethanol or 10% sodium dodecyl sulfate. Under combined treatment with guanidinium hydrochloride at low pH (1.5) or upon heating (>70° C.) in the presence of denaturing agents or detergents, the protein is denatured, and biotin is dislodged from the disrupted binding site.

Avidin recognizes biotin mainly at the ureido (urea-like) ring of the molecule. The interaction between the binding site of avidin with the sulfur-containing ring of the valeric acid side chain of the vitamin is of much lower strength. The relatively weak interaction between the carboxy-containing side chain of biotin and avidin means that the former can be modified chemically and attached to a wide variety of biologically active material; the biotin moiety of the resultant derivative or conjugate is still available for interaction with avidin. In turn, the avidin can be derivatized with many other molecules, notably "probes" or reporter groups of different types.

This is the crux of avidin-biotin technology (Wilchek and Bayer, 1990). Thus, a biologically active target molecule in an experimental system can be "labeled" with its biotinylated counterpart (a binder), and the product can then be subjected to interaction with avidin, either derivatized or conjugated with an appropriate probe.

The use of the egg-white avidin in the avidin-biotin technology is sometimes restricted due to the high basicity (pI 10.5) and presence of sugar moieties on the avidin molecule, which may lead to nonspecific or otherwise undesired reactions. In recent years, the bacterial protein, streptavidin, has largely replaced egg-white avidin for most applications in avidin-biotin technology. However, the problems with streptavidin (high cost and biotin-independent cell binding) have prompted renewed interest in egg-white avidin as the standard for avidin-biotin technology. For this purpose, modified avidins exhibiting improved molecular characteristics both over the native protein (and previous derivatives thereof) as well as over streptavidin, have been prepared, such as N-acyl avidins, e.g., N-formyl, N-acetyl and N-succinyl avidins. These derivatives of avidin reduce the charge of the protein, but they are all prepared via covalent attachment to the available lysines of avidin, and the consequent blocking of the free amino groups hinders subsequent preparation of other types of conjugates (notably protein-protein conjugates such as avidin-labeled enzymes) which are often prepared by crosslinking via lysine residues using bifunctional reagents (e.g. glutaraldehyde).

A more useful and effective alternative to lysine modification is the modification via arginines. In this case, the pI of the protein is efficiently reduced and the lysines are still available for subsequent interaction. Two different derivatives of avidin which are modified in this manner are commercially available. One, ExtrAvidin®, can be obtained in various functionally derivatized or conjugated forms from Sigma Chemical Company (St. Louis, Mo.). A second, NeutraLite Avidin™ (a product of Belovo Chemicals, Bastogne, Belgium) is additionally modified and can be purchased in bulk quantities.

Although the reduction of the pI of egg-white avidin solves one of the problems, the presence of the oligosaccharide residue remains a serious source of nonspecific (biotin-independent) interaction which restricts its application. The return of egg-white avidin as the standard for avidin-biotin technology has been contingent upon the removal of its sugars. The possibilities for removing a sugar from a glycoprotein are quite limited; it is possible to do so either chemically or enzymatically. The chemical methods currently available, e.g., using HF or periodate oxidation, are either destructive or inefficient. The well known enzymatic method, which employs N-glycanase, is usually very expensive and not very effective for avidin when conventional methodology is used. Eventually, a viable procedure for deglycosylation was established and the resultant product was subsequently modified chemically via the arginines and is known under the trade mark NeutraLite Avidin™ (Belovo Chemicals).

In spite of all these improvements, one of the main problems in the several applications of the avidin-biotin technology is the lack of an appropriate labeled avidin to permit the follow up of the binding of avidin to biotinylated compounds.

In addition to its interaction with biotin, avidin is known to associate non-covalently also with 4'-hydroxyazobenzene-2-carboxylic acid at the same biotin-binding site of the protein, but with a lower affinity (~10$^{-5}$–10$^{-6}$ M) (Green, 1965). This non-covalent association is accompanied by a change in color from yellow to red (350 nm to 500 nm), thus allowing determination of avidin and its free binding sites.

Derivatives of 4'-hydroxyazobenzene-2-carboxylic acid and conjugates thereof with oligo and macromolecular carriers (HABAylated molecules) are the subject of copending application of Applicants filed at the same date as the present application.

SUMMARY OF THE INVENTION

It has now been found in accordance with the present invention that certain HABA derivatives covalently bound to avidins, preferably at the binding site, form red colored HABAylated avidins (red avidins) that change the red color to yellow upon binding biotin. The displacement of the HABA moiety out of the binding site by biotin is due to a higher affinity of biotin to the red colored avidin.

The present invention thus relates, in one aspect, to covalent conjugates of 4'-hydroxyazobenzene-2-carboxylic acid derivatives (hereinafter HABA) and an avidin-type molecule, these conjugates referred herein as "HABAylated avidins", of the formula:

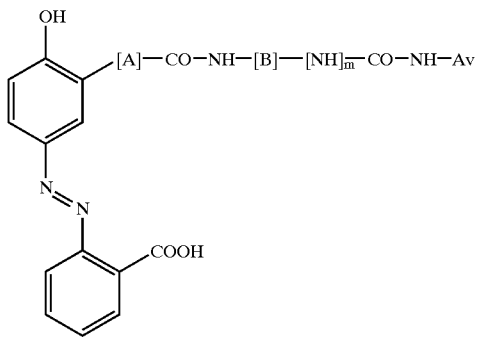

wherein

A is $(CH_2)_n$ or —CH=CH—, wherein n is an integer from 0–10;

B is $(CH_2)_n$ wherein n is an integer from 2 to 10;

m is zero or 1; and

Av is the residue of an avidin-type molecule selected from the group comprising native egg-white avidin, recombinant avidin, deglycosylated avidins, bacterial streptavidin, recombinant streptavidin, truncated streptavidin and other derivatives of said avidin-type molecules.

When the HABA moiety is inside the avidin binding pocket, it has the quinone conformation, the conjugate has a red color and $\lambda_{max}$=504 nm: this is the HABAylated red avidin. When the HABA moiety is expelled from the avidin binding pocket by biotin, it has the azo configuration, the conjugate has a yellow color and $\lambda_{max}$=356 nm: this is the HABAylated yellow avidin (see Appendix A). In the specification and claims herein, the term "HABAylated avidin" comprises both the azo and the quinone conformations.

In the HABAylated avidins according to the invention, A is preferably —CH$_2$—CH$_2$— or —CH=CH—, and B is preferably $(CH_2)_2$, $(CH_2)_5$ or $(CH_2)_6$.

The HABAylated avidins of the invention are prepared by reaction of an avidin-type molecule with a succinimidyl ester or carbamate of HABA derivatives of formulas I and II, respectively, or a cyclic derivative of formula III:

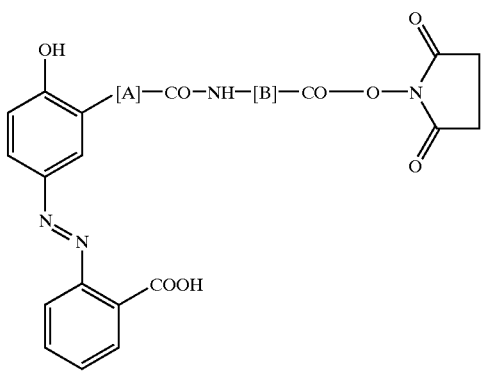

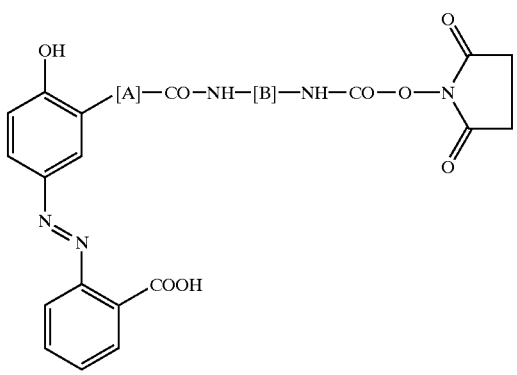

-continued

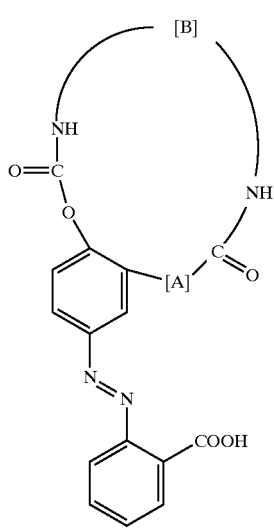

III wherein A is $(CH_2)_n$ or —CH=CH—, wherein n is an integer from 0–10; and B is $(CH_2)_n$ wherein n is an integer from 2 to 10.

The HABA compounds of formulas I and II are the subject of copending PCT application of Applicants filed at the same date as the present PCT application. The cyclic derivatives of formula III are encompassed by the present invention.

The invention further relates to columns containing immobilized HABAylated avidins, attached to a solid support or matrix.

In another aspect, the invention relates to a single-layer protein system comprising:
(i) a protein:
(ii) two ligands I and II which bind with different affinities at the same binding site of said protein, said ligand I being the low affinity ligand and said ligand II being the high affinity ligand: and
(iii) a molecule that recognizes the low affinity ligand I, wherein in said single-layer protein system the high affinity ligand II is buried within the binding site of the protein (i) and the low affinity ligand I is covalently bound to the protein and associated with the molecule (iii) that recognizes it.

In one embodiment of the single-layer protein system aspect, the molecule (iii) may be labeled with high affinity ligand II.

In another aspect, the invention relates to a multilayer protein system comprising two or more layers of the single-layer protein system. In the last layer of the multilayer protein system, the molecule (iii) is preferably not labeled with high affinity ligand II.

In one preferred embodiment, the protein (i) in the single-layer or multilayer protein systems is an avidin-type molecule selected from the group comprising native egg-white avidin, recombinant avidin, deglycosylated avidins, bacterial streptavidin, recombinant streptavidin, truncated streptavidin and other derivatives of said avidin-type molecules; the low affinity ligand I is HABA (4'-hydroxyazobenzene-2-carboxylic acid) or a HABA derivative, the high affinity ligand II is biotin, and the molecule (iii) that recognizes ligand I is an anti-HABA antibody or a biotinylated anti-HABA antibody.

The anti-HABA antibody used according to the invention may be polyclonal or monoclonal, and can be prepared by immunization of rabbits and mice, respectively, with a conjugate of HABA and an immunogenic protein, such as for example HABA-KLH. The anti-HABA antibodies are the subject of copending application of Applicants filed at the same date as the present application.

In another embodiment, the protein (i) in the single-layer or multilayer protein system is anti-dinitrophenyl (DNP)-antibody; the low affinity ligand I is trinitrobenzene (TNP) or mononitrobenzene (MNP), the high affinity ligand I is DNP and the molecule (iii) that recognizes ligand I is a MNP- or TNP-tagged anti-DNP antibody.

The single-layer or multilayer protein system according to the invention may be formed on a substrate such as gold, silicium, polystyrene. Preferably, the multilayer protein system will comprise 5–6 layers.

In another aspect, it is provided a method for assembling a single-layer protein system according to the invention, which comprises the steps of:
(a) covalently binding said low affinity ligand I to said protein (i), thus obtaining a low affinity ligand I-protein (i) complex in which said ligand I is buried within the binding site of said protein (i) and is thus not available for interaction with other molecules that recognize it;
(b) reacting the high affinity ligand II or a compound containing said high affinity ligand II with the low affinity ligand I-protein (i) complex of step (a) above, whereby low affinity ligand I is expelled from within the binding site to the periphery but remains covalently bound to protein (i) and high affinity ligand II is associated to, and buried within, the binding site of protein (i); and
(c) reacting the low affinity ligand I-protein(i)-high affinity ligand II complex of step (b) with a molecule (iii) that recognizes and binds to low affinity ligand I and can be labeled with high affinity ligand II.

In still another aspect, it is provided a method for assembling a multilayer protein system according to claim 3, which comprises the steps of:
(a) covalently binding said low affinity ligand I to said protein (i), thus obtaining a low affinity ligand I-protein (i) complex in which said ligand I is buried within the binding site of said protein (i) and is thus not available for interaction with other molecules that recognize it;
(b) reacting the high affinity ligand II or a compound containing said high affinity ligand II with the low affinity ligand I-protein (i) complex of step (a) above, whereby low affinity ligand I is expelled from within the binding site to the periphery but remains covalently bound to protein (i) and high affinity ligand II is associated to, and buried within, the binding site of protein (i);
(c) reacting the low affinity ligand I-protein(i)-high affinity ligand II complex of step (b) with a molecule (iii) that recognizes and binds to low affinity ligand I and is labeled with high affinity ligand II; and
(d) reacting the protein system of step (c) with low affinity ligand I-protein (i) complex as in step (b) above, and repeating steps (c) and (d) as desired.

DETAILED DESCRIPTION OF THE INVENTION

Figure 1:
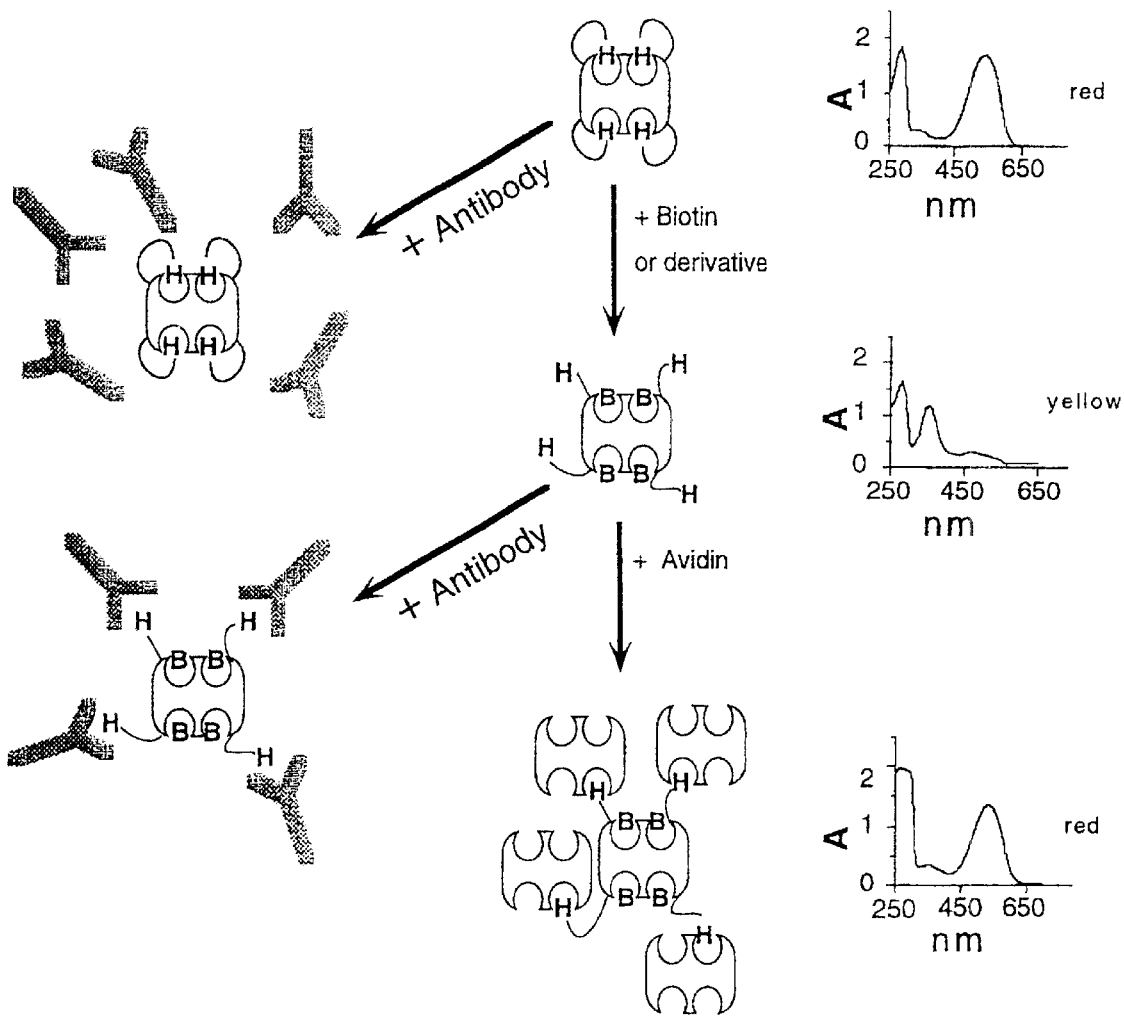
FIG. 1 is a schematic depiction of the signaling system according to the invention. HABAylated red avidin (⊢⊣), $\lambda_{max}$=504 nm (see red spectrum on the right side) does not interact with the anti-HABA antibody (—◁). The cascade is triggered upon addition of biotin (B) or biotin-containing molecules, which expel the covalently attached HABA moiety (H) from the binding site. The spectrum shows a shift to yellow, $\lambda_{max}$=356 nm. The HABA group is now available for subsequent interaction with anti-HABA antibody or avidin. Reaction with avidin restores the red color.

The term "avidin-type molecule" as used herein refers to the native egg-white glycoprotein avidin, to deglycosylated forms of avidin, to bacterial streptavidins produced by selected strains of Streptomyces, e.g., Streptomyces avidinii, to truncated streptavidins, and to recombinant avidin and streptavidin as well as to derivatives of native, deglycosylated and recombinant avidin and of native, recombinant and truncated streptavidin, for example, N-acyl avidins, e.g., N-acetyl, N-phthalyl and N-succinyl avidin, and the commercial products ExtrAvidin and Neutralite Avidin.

All forms of avidin-type molecules are encompassed by the present invention, both native and recombinant avidin and streptavidin as well as derivatized molecules, e.g. nonglycosylated avidins, N-acyl avidins and truncated streptavidins. Some of these materials are commercially available, e.g. native avidin and streptavidin, nonglycosylated avidins, N-acyl avidins and truncated streptavidin, or can be prepared by well-known methods (see Green, 1990, for preparation of avidin and streptavidin; Hiller et al., 1990, for preparation of non-glycosylated avidin; Bayer et al., 1990, for the preparation of streptavidin and truncated streptavidin). Recombinant avidin and streptavidin can be prepared by standard recombinant DNA techniques, for example, as described by Chandra and Gray, 1990, for recombinant avidin, and by Argarana et al., 1986, for recombinant streptavidin.

The "biotinylated ligands" that can be used with the modified avidins of the invention in methods of application of the avidin-biotin technology, are biotinylated forms of desired ligands such as proteins, e.g. antibodies, enzymes, lectins, or carbohydrates and glyco-conjugates, e.g. glycoproteins, gangliosides, heparin, polysaccharides, or nucleic acids, i.e. DNA and RNA, or phages, viruses, bacteria and other cells, wherein said ligands are covalently linked to biotin or to a homologue, analog or derivative thereof. Many biotinylated ligands are commercially available or can be prepared by standard methods (see, for example, Bayer and Wilchek, 1992).

HABAylated avidins as described in the invention can be used as very sensitive tools for the recognition and visualization of biotin and biotinylated molecules. They can replace avidin in all the applications of the avidin-biotin technology where avidin-like molecules are currently used (molecular and cell biology, biochemistry and diagnostics) with the main advantage of providing a strong signal enhancement with minimum background.

The concept behind the use of this new colored avidin is the fact that, when biotin or biotin-containing molecules are added, the HABA moieties, while remaining covalently linked to the avidin molecule, are expelled from the binding pocket and remain available at the avidin surface. After binding of biotin, the HABA moieties are used as tags for the following addition of anti-HABA antibodies (labeled or non-labeled). Both the HABAylated avidin and/or the anti-HABA antibodies can be labeled with biotin or its derivatives, different chromophores or enzymes, thus allowing visualization of the complex formed. Biotin or biotin-containing molecules can be used to expel only parts of the HABA from the red avidin, leaving the other HABA residues still buried in the binding site. It is important to note that, upon biotin binding to the HABAylated avidin, the HABA molecules shift from the quinone to the azo conformation (see Appendix A) and a color change from red to yellow is observed.

The invention also relates to a HABAylated avidin-type molecule of the invention attached to a solid support or matrix. Any solid support used in the art is suitable such as, but not limited to, resins, microtiter plates, glass beads, magnetic beads and the like. The attachment of the HABAylated avidin to the solid support may be covalent or noncovalent and is carried out by standard methods. In one preferred embodiment, the HABAylated avidin-type molecule is immobilized onto a resin, preferably Sepharose, and the thus obtained Sepharose-HABAylated-avidin affinity resin may be poured into a column for isolation procedures (Bayer and Wilchek, 1992). In the description herein the term "avidin-Sepharose column" will be used for a column that contains a HABAylated avidin-type molecule of the invention immobilized onto a Sepharose resin. These columns are useful particularly for separation procedures.

In another embodiment of the invention, the HABAylated avidin-type molecule is attached to wells of microtiter plates.

The red HABAylated avidins of the invention can be used for the determination of biotinylated sites on proteins. They also permit to follow visually the attachment of avidin to biotinylated molecules, which has not been possible as yet. The binding of the HABAylated avidin to biotin-containing molecules can also be monitored with anti-HABA e antibodies, both monoclonal and polyclonal, thus providing an additional means for detection and a convenient tool for application using the avidin-biotin system.

The anti-HABA antibodies are the subject of a copending application filed on the same date and are of two categories: antibodies that recognize the HABA moiety on any protein including avidin, and those that recognize the HABA moiety on avidin only after the addition of biotin or biotinylated protein (i.e., after exposing the HABA moiety). However, the second type of antibody can develop the binding cascade in a very specific and ordered way. The first type of antibody, being less specific, can recognize HABA when it is either inside or outside the avidin pocket and it does not allow such a delicate control over the amplification cascade.

According to the present invention, it could be determined that protein cascades or multilayers of proteins can be formed artificially, whereby the binding of one molecule depends on the signaling of another. Such a system can be achieved using two molecules which display differing affinities for the same binding site of a protein, such as biotin and HABA for avidin, or dinitrobenzene and tri-(or mono) nitrobenzene for anti-dinitrophenyl antibody. If the lower-affinity ligand (e.g. HABA or tri-(or mono)nitrobenzene) is coupled covalently to the binding site, the high-affinity ligand (e.g. biotin or dinitrobenzene) can be used to displace it from the binding pocket. The expelled moiety, still covalently attached to the protein, is now available for further interaction with other molecules that can bind to this low-affinity ligand (e.g. optionally biotinylated anti-HABA antibody or optionally MNP- or TNP-tagged anti-DNP antibodies). Consequently, one interaction will be dependent on the previous one, thus enabling to trigger a cascade of binding, i.e., to construct an organized system of protein multilayers, thereby increasing the signal tremendously.

The possibility of building organized protein layers only in biotinylated sites of a surface can be a great advantage in many biophysical applications such as in protein chips, biosensors, etc.

The invention will now be illustrated by the following non-limiting examples.

EXAMPLES

LIST OF COMPOUNDS

In the Examples, the following compounds 1–11, which formulas are presented in Appendix B hereinafter Gust before the claims), will be identified by their numbers in bold. Compounds 8, 10 and 11 are used as starting materials for the preparation of the HABAylated avidins. Compounds 11 are part of the present invention.

0. 4'-hydroxyazobenzene-2-carboxylic acid (HABA)
1. 3-(2-hydroxyphenyl)propionic acid A=$(CH_2)_2$
2. N-succinimidyl 3-(2-hydroxyphenyl)propionate A=$(CH_2)_2$
3. N-6-(t-butoxycarbonylamino)hexyl 3-(2-hydroxyphenyl) propionamide A=$(CH_2)_2$; B=$(CH_2)_6$
4. N-6-(methoxycarbonyl)pentyl 3-(2-hydroxyphenyl) propionamide A=$(CH_2)_2$; B=$(CH_2)_5$
5. N-5-carboxypentyl 3-(2-hydroxyphenyl)propionamide A=$(CH_2)_2$; B=$(CH_2)_5$
6. 3'-(6-t-butoxycarbonylamino)hexylaminocarbonylethyl-4'-hydroxy-azobenzene-2-carboxylic acid A=$(CH_2)_2$; B=$(CH_2)_6$
7. 3'-(6-aminohexylaminocarbonylethyl)4'-hydroxy-azobenzene-2-carboxylic acid A=$(CH_2)_2$; B=$(CH_2)_6$
8. 3'-(6-(succinimidyloxycarbonylamino) hexylaminocarbonylethyl)4'-hydroxy-azobenzene-2-carboxylic acid A=$(CH_2)_2$; B=$(CH_2)_6$
9. 3'-(5-carboxypentylaminocarbonylethyl)-4'-hydroxy-azobenzene-2-carboxylic acid A=$(CH_2)_2$; B=$(CH_2)_5$
10. 3'-(5-succinimidyloxycarbonylpentylaminocarbonylethyl)4'-hydroxy-azobenzene-2-carboxylic acid A=$(CH_2)_2$; B=$(CH_2)_5$
11. cyclic HABAs ABBREVIATIONS: BCA: bicinchoinic acid; BOC: t-butoxycarbonyl; BSA: bovine serum albumin; DCC: N,N'-dicyclohexylcarbodiimide; DG-avidin: deglycosilated avidin; DMAP: dimethylaminopyridine; DMF: N,N'-dimethyl formamide; DSC: disuccinimidylcarbonate; HABA: 4'-hydroxyazobenzene-2-carboxylic acid; KLH: Keyhole Lympet Hemocyanin; NHS: N-hydroxysuccinimide; Su: succinimidyl; TEA: triethylamine; TPCK: L-1-Tosylamide-2-phenylethylchloromethylketone; TSTU: tetramethyluronium tetrafluoroborate.

MATERIALS AND METHODS (i) Materials. Triethylamine (TEA) and N,N-dicyclohexylcarbodiimide (DCC) were obtained from Merck (Darmstadt, Germany), N-BOC-1,6-diaminohexane and TSTU were obtained from FLUKA, (Buchs, Switzerland), disuccinimidylcarbonate (DSC) was purchased from Calbiochem (La Jolla, CA USA); 3(2-hydroxyphenyl)propionic acid and anhydrous hydrochloric acid solution in dioxane were purchased from Aldrich (Milwaukee Wis., USA). Egg-white avidin was provided by STC laboratories (Winnipeg, Canada), deglycosilated avidin (DG-avidin) by Belovo (Bastogne, Belgium) and streptavidin by Boehringer Mannheim (Mannheim, Germany). DG-avidin was prepared according to the procedure of Hiller, 1990. N-hydroxysuccinimide, biotin, HABA, BSA, TCPK treated trypsin, Keyhole Lympet Hemocyanin (KLH) and all the other chemicals were obtained from Sigma Chemicals (St. Louis, Mo., USA). Sepharose CL4B and Sephadex G25 was purchased from Pharmacia Biotech AB (Uppsala, Sweden) Peroxidase-conjugated anti-rabbit IgGs were obtained from Jackson ImmunoResearch (West Grove, Pa., USA). UV spectra were recorded with a Milton Roy spectroric UV-Vis spectrophotometer, mod. 1201; HPLC analysis was carried out on a Vidac 'Protein and Peptides $C_{18}$' column, using a Waters pumping system 600E, a Knaur variable wavelength detector and a Hewlet Packard model 3390A integrator.

(ii) Biotinylation Procedures. The proteins and enzymes used in the Examples were biotinylated by conventional biotinylating methods using biotinyl N-hydroxysuccinimide ester (BNHS) as described previously (Bayer and Wilchek, 1990).

(iii) Enzyme assays. Horseradish peroxidase activity (HSP). Peroxidase activity was determined using o-phenylenediamine (oPD) as substrate. Substrate solution included 8 mg of the substrate per 20 ml in citrate-phosphate buffer (50 mM), pH 5, to which 10 $\mu$l of 30% hydrogen peroxide was added. The reaction was stopped using 1M $H_2SO_4$. Color formation was measured at 490 nm.

(iv) Protein. Protein was determined by the Bradford method using either avidin or streptavidin (where appropriate) or BSA as a standard. HABAylated protein was determined using the BCA assay (Pierce, Rockford, Ill, USA).

Example 1

Synthesis of Compound 10

1.1 Synthesis of Compound 4

To a solution of Compound 1 (0.997 g, 6 mmol) in $CH_2Cl_2$ (25 ml) were added ε-aminocaproic acid methyl ester (1.74 g, 12 mmol), an equimolar amount of TEA (1.6 ml, 12 mmol) and DCC (1.36 g, 6.6 mmol). The reaction was carried out for 4 hours in an ice bath. The solution was washed thoroughly with water, HCl (0.05 M), water, bicarbonate (0.1 M) and again with water. The $CH_2Cl_2$ fraction was dried over sodium sulfate and the pure product Compound 4 was obtained by precipitation with absolute diethylether.

1.2 Synthesis of Compound 5

Compound 4 (330 mg, 1.08 mmol) was dissolved in methanol and 5.4 ml 0.5 M NaOH were added thereto. After 1 hour, the reaction mixture was brought to pH 2 with HCl and the methanol removed by evaporation. The oily mixture was dissolved in hot ethyl acetate and the pure product Compound 5 crystallized upon cooling down.

1.3 Synthesis of Compound 9

Compound 9 was synthesized from the Compound 5 following the same procedure described in Example 2.3 below for Compound 6.

1.4 Synthesis of Compound 10

Compound 10 was prepared from Compound 9 by two different procedures:

a. Activation with NHS

The synthesis was carried out using the same procedure described in Example 2.1 below for Compound 2. Compound 9, DCC/CH$_2$Cl$_2$ and NHS were used in equimolar concentrations to avoid activation of the carboxyl group at the second phenyl ring. The urea derivative was removed by filtration, and Compound 10 was washed with water and dried.

b. Activation with TSTU (Bannwarth, 1991)

TSTU (70.4 mg, 0.24 mmol) and DMAP (57 mg, 0.48 mmol) were added to Compound 9 (100 mg, 0.24 mmol) dissolved in a mixture of DMF/dioxane/water (1/1/0.5). After complete conversion (30 min), Compound 10 (purity 96%) was lyophylized and further purified by HPLC.

1.5 Synthesis of analogs of Compound 10

The same synthesis was successfully carried out for a compound wherein A is —CH=CH= using 2-hydroxycinnamic acid as the starting compound in the first step instead of Compound 1. Other HABA derivatives can be obtained from similar hydroxyphenyl reagents carrying different spacer arms in position 2.

Example 2

Synthesis of Compound 8

2.1 Synthesis of Compound 2

To a cooled solution of Compound 1 (0.997 g, 6 mmoles) in CH$_2$Cl$_2$ (21 ml), NHS (0.828 g, 7.2 mmoles) and DCC (1.485 g, 7.2 mmoles) were added. After 3.5 h, the solution containing Compound 2 was filtered and directly used for the next synthetic step, without any further purification.

2.2 Synthesis of Compound 3

N1-BOC-1,6-diaminohexane (1.52 g, 6 mmoles) was added, while stirring, to the dichloromethane solution of Compound 2, followed by 835 µl (6 mmoles) of TEA. The reaction was stirred overnight at room temperature, filtered and evaporated to dryness. The product was redissolved in ethyl acetate and the organic solution was washed (with diluted NaHCO$_3$, diluted citric acid and water), dried over Na$_2$SO$_4$ and evaporated to dryness. Diethyl ether (30 ml) was added to the resulting oil, the precipitated impurities were removed by filtration, and the solution containing Compound 3 was evaporated to dryness and used further.

2.3 Synthesis of Compound 6

To cooled anthranilic acid (0.750 g, 5.45 mmoles) and NaNO$_2$ (0.377 g, 5.45 mmoles) dissolved in water (15 ml), 1.5 ml of concentrated HCl were added. After 10 min, the solution was dropwise added to Compound 3 (1.62 g, 5.45 mmoles) dissolved in a mixture of methanol:0.5M KOH , 1:1 (15 ml). The pH was controlled and adjusted to 8.0 using HCl and KOH. After 20 min, methanol was removed by evaporation, the solution was acidified to pH 3–4 with diluted citric acid, and the solid product was extracted with ethyl acetate. The organic solution was washed with water, dried over Na$_2$SO$_4$ and evaporated to dryness, thus obtaining Compound 6.

2.4 Synthesis of Compound 7

A solution of Compound 6 in dioxane was dried, filtered, and HCl saturated dioxane was added. After 1 hour, the product Compound 7 precipitated as the hydrochloride salt, was isolated by filtration, washed with diethyl ether and dried.

2.5 Synthesis of Compound 8

A solution of Compound 7 (35.8 mg, 0.08mmoles) in DMF (0.24 ml) was slowly added into portions (8×30 ?l), while stirring, to a solution of DSC (41 mg, 0.16 mmoles) in CH$_3$CN (1.6 ml). After each addition, 2 equivalents of TEA (with respect to Compound 7) were also added, and the pH monitored continuously and maintained below 4.0. Five minutes after the last addition of the HABA-derivative 7, 2 ml of IN HCl were added. The product Compound 8 crystallized as a fine powder. It was isolated by filtration, washed with diluted HCl and dried.

Example 3

Synthesis of Compound 11

The synthetic pathway leading to Compound 11, the cyclic form of HABA, via Compound 8, is represented in Scheme 2.

Compound 11 is readily obtained from Compound 8 in neutral aqueous buffer. A concentrated DMF solution of Compound 8 (10 mg/ml) is diluted in PBS and pH is adjusted to 8.0 with small additions of 4% NaHCO$_3$. Transformation of the active carbamate 8 into the cyclic HABA derivative 11 is verified by TLC (CHCl$_3$/MeOH 20%) and UV spectrophotometry. In the conditions used, total conversion is obtained after 24 hours standing at room temperature.

Example 4

Preparation of HABAvlated Avidins

Avidin-type molecules were affinity labeled with HABA reagents 8, 10 and 11. The cyclic Compound 11 was designed such that the HABA moiety would remain covalently attached to the binding site of avidin. The ortho position of the HABA hydroxy group was thus modified with a reactive functional group, which, due to steric constraints, forms an intramolecular cyclic carbamate (Scheme 1). This cyclic HABA 11 is hydrolyzed by avidin enabling exploitation of the principle of forced catalytic hydrolysis (Vetter et al., 1994) to attach the HABA moiety to an appropriate site in or near the binding site of avidin. In the conditions used, only the primary amino group directly involved in the pseudo-enzymatic reaction (Lys 111 in avidin) can be derivatized with this reagent. The cyclization of the reagent was necessary since the activated linear N-hydroxy-succinimidocarbamate would react with any amino group, whereas the cyclic compound reacts in situ, i.e., selectively, after occupying the binding site of avidin. This results in a red HABAylated avidin that is labeled with 4 HABA molecules occupying the 4 binding sites of avidin.

Reagents 8 and 10 are less specific. These HABA derivatives which are activated as N-succinimidyl carbamate and N-succinimidyl ester, respectively, react with primary amino groups at the level of any protein, peptide or amino-carrying polymer surface. Binding occurs through any primary amino function, therefore, they can react with any lysine on the avidin/streptavidin surface. In this case, coupling in the area of the (strept)avidin's biotin/HABA binding pocket occurs as in a conventional labeling, where the affinity for a specific site of the protein is directing the site of labeling. Additional labeling at the periphery of the avidin will result in an additional peak at 357 nm. Binding of anti-HABA antibodies to HABA will be independent of biotin for the HABA moiety outside of the binding pocket at the periphery and biotin-dependent for the HABA bound inside the binding pocket. This HABA must be expelled from the binding site by addition of biotin prior to their binding to the antibodies.

4.1 HABAylation of Avidin With Compound 8

10–50 ml of a concentrated solution of Compound 8 in DMF (5–30 mg/ml) were added, while stirring, to a solution of an avidin-type molecule in aqueous buffer at pH 8.0–8.5 (2–10 mg/ml). The molar ratio between the HABA-succinimidyl carbamate derivative 8 and the avidin-type molecule was between 50 and 400, depending on the starting avidin concentration and the desired degree of modification. The reaction was carried out at room temperature or lower for 1–2 hours.

4.2 HABAylation of Avidin With Compound 10

A freshly prepared solution of HABA-N-succinimidyl ester 10 (2.5 ml) in EtOH:PBS, 1:3 (1–50 mg/ml) was added, while stirring, to a solution of an avidin-type molecule (2–20 mg) in 1 ml of phosphate buffer, pH 7.4 containing 0.5M NaCl. The molar ratio between the ester derivative and the avidin-type molecule was between 4 and 100 depending on the starting protein concentration and the desired degree of modification Addition of the HABA resulted in an immediate shift of the spectrum to 504 nm. The reaction was carried out at room temperature for 2–3 hours. HABAylations were carried out using egg-white avidin, streptavidin, Neutralite avidin and DG-avidin. cl Example 5

HABAylation of Avidin With Compound 11

5.1 Preparation

Figure 2:
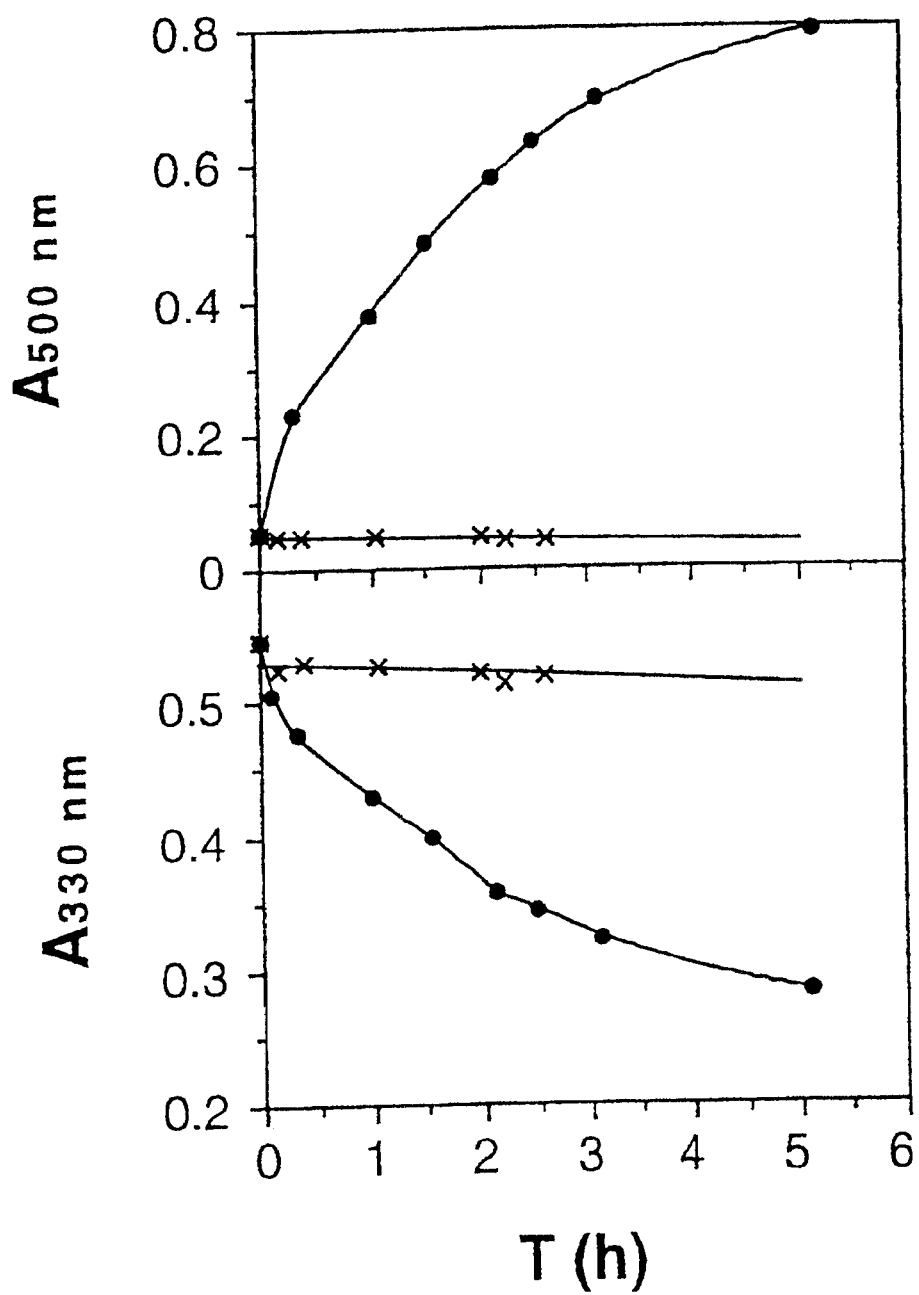
FIG. 2 illustrates the reaction of avidin with the cyclic HABA-derivative (Compound 11) in the presence (×) or absence (●) of biotin. Avidin was incubated with an equimolar (per subunit) concentration of the cyclic HABA in aqueous buffer at pH 8, and the change in absorbance at 500 and 330 nm was followed spectrophotometrically.

Compound 11, prepared from Compound 8, was added to an avidin solution in PBS. A shift in the spectrum to 504 nm was observed that develops gradually. The same effect was observed for deglycosylated avidin, Neutralite avidin and streptavidin. The reaction at room temperature was monitored by UV and followed by measuring either absorbance at 500 and 331 nm, or the ratio between them, as parameters. When no further change in those parameters was observed, the modified avidin was purified from excess reagent by gel filtration. Different reaction conditions varying either the protein concentration (0.8–3 mg/ml) or the HABA/subunit ratio (between 1 to 10) have been used and the same final product, containing one HABA/subunit, was obtained. High protein concentration as well as high HABA/subunit ratios allow faster reactions. As shown in FIG. 2, no shift was observed if the cyclic reagent 11 was added together with biotin (x), indicating that biotin occupied the binding site and prevented the reaction with HABA.

5.2 Characterization 5.2.1 Concentration of HABA-labeled Avidin

Affinity labeling with HABA influences the absorbance of avidin in the 280 nm area. Therefore, avidin molar extinction constant at 280 nm ($\epsilon^{1\%}_{280\ nm}$ 32 15.4) cannot be used to determine the concentration of the HABA-labeled avidin derivative. The most commonly used color reagents for determination of protein concentration are also affected by the HABA molecule. Among the methods tested, the BCA protein assay, even if not accurate, proved to be the most reliable one. $\epsilon^{1\%}_{280\ nm}$ of a fully HABAylated avidin with Compound 11 was calculated from a series of experiments as being 21.9. Molar extinction value of HABA inside the complex pocket was determined to be $\epsilon_{504\ nm}[cm^{-1}M^{-1}]$= 33,000. If complete HABAylation is obtained, this value can also be used to assess the concentration of the avidin-HABA conjugate.

5.2.2 Spectrophotometric Characterization

UV spectrum of the purified affinity HABA-labeled avidin obtained with compound 11 was recorded. As shown in FIG. 1, the HABAylated-avidin shows a maximum at 504 nm. After addition of biotin, the HABA moiety is expelled from the binding site resulting in a shift of color from red to yellow $\lambda_{max}$=356 nm). Addition of avidin restores the red color and the maximum shifts back to 504 nm.

5.2.3 Number of HABA Molecules/Avidin Subunits and Localization of the HABA

HABA-labeled avidin-type molecules carry one single HABA molecule per protein subunit. Precise determination of the number of HABA molecules/avidin subunit was assessed by mass spectrometry on a labeled DG-avidin sample (not shown). The analysis of the non-HABAylated DG-avidin showed an ml/z value of 14287–14290, corresponding to a single subunit of DG-avidin. The HABAylated DG-avidin showed a single peak (m/z 14727–14734), the difference in mass (about 440 units) being consistent with the molecular weight of the HABA moiety.

To determine which amino acid residue of the DG-avidin molecule was modified by HABA, the HABAylated DG-avidin was subjected to trypsin digestion. The hydrolysate was separated by HPLC, and the sequence of the orange-colored HABAylated peptide was analyzed. The analysis showed that the Lys-111 residue was HABA-modified.

5. 2.4 Stability and storage of the HABA-labeled Avidins.

Avidins are known for their good stability. Similarly, the affinity HABA-labeled avidins obtained according to the invention are very stable:

PBS or neutral pH solutions of HABAylated-avidins can be stored at 4° C. for several months if kept in a sterile environment;

Complete heat denaturation of HABAylated-avidins in PBS solution requires more than 2 hours treatment at 100° C.

The HABAylated-avidins can be freeze-dried for long term storage either from PBS or salt free solution. Original solutions can be readily re-obtained upon addition of the proper buffer.

Short term standing (1 hour) at high (0.1N NaOH) or low pH (0.1 M acetic acid) do not damage the HABAylated-avidins.

Example 6

Labeling of HABAvlated Avidins With Non-HABA Markers

Since only one lysine per subunit is covalently modified by HABA in the affinity HABAylated avidin (see Example 5.2.3 above), the other primary amino functions on the protein surface are available for further coupling. Thus, other labels such as fluorescent, chemiluminescent, dye molecules or enzymes can be covalently linked to the HABAylated-avidin molecule by procedures used for general protein non-radiaoctive labeling (Garman, 1997). According to the invention, the HABAylated-avidin of previous examples was further labeled with FITC, a fluorescent molecule, and with the dye dinitrobenzene (DNP), Analysis of the resulting products showed that the FITC and DNP moieties were covalently linked to other amino groups of the HABAylated avidin molecule.

Example 7

Anti-HABA Antibodies 7.1 Preparation of Immunogenic HABAylated Proteins

KLH, BSA, and goat-affinity purified anti-Mouse IgGs were HABAylated using the succinmidyl reagents (Compound 8, 10) as coupling agent by the procedure described in Example 4.1 above for avidin. Briefly, the coupling agent dissolved in DMF was added to a solution of the protein in 0.1M $NaHCO_3$ (2–10 mg/ml). After 2 hours, the excess of HABA reagent was removed by gel filtration on a G25 column. The degree of coupling could be estimated from the UV spectra of the conjugates, considering the $\epsilon_{356}$ of 12,900 for the HABA-derivative in PBS and measuring the protein concentration by BCA protein assay.

7.2 Preparation of anti-HABA Polyclonal Antibodies

Rabbits (12 weeks) were immunized by intradermal injection of 0.5 mg of HABA-KLH (carrying ~50 molecules of HABA/protein) emulsified in complete Freund's adjuvant. Boosts were administered after 4 weeks by injecting 0.5 mg of HABA-KLH in incomplete Freund's adjuvant. Blood was collected from the ear vein two weeks after boosting and serum was isolated by centrifugation and preserved at −20° C. Preserum was collected before immunization and used as a control.

7.3 Affinity Purification of Anti-HABA Polyclonal Antibodies

Two different Sepharose gels (A and B) were prepared for the isolation of anti-HABA antibodies specific to different epitopes in the HABA molecule. A schematic representation of the two gels is described in Scheme 2.

GEL A is a highly functionalized HABAylated-Sepharose having the correct HABA moiety (4'-hydroxy-azophenyl-2-carboxylic acid linked at position 3') connected with a spacer arm in a similar way as in the HABAylated KLH.

GEL B is a highly functionalized gel having a HABA moiety with a slightly different structure (2'-hydroxy-azophenyl-2-carboxylic acid linked at position 5' via a spacer arm) obtained by diazotization of tyramine-Sepharose with anthranilic acid.

These two gels allow isolation of anti-HABA antibodies with different characteristics: GEL A is able to isolate anti-HABA antibodies that recognize the whole HABA molecule, while GEL B allows the isolation of antibodies that are specific for the azophenyl-2-carboxylic acid moiety of the HABA core.

7.4.a Preparation of GEL A

Sepharose CL-4B hydroxyl functions were first activated as p-nitrophenyl carbonates (Wilchek et al, 1984) and the active gel was then coupled to a 2-hydroxyphenyl derivative carrying a spacer arm with a primary amine as the terminal group. Different spacers can be introduced by varying this first compound. The HABA function was then obtained by diazotization of the phenyl residues directly on the Sepharose support (Vetter et al, 1994).

(i) Sepharose-tyrosine or 2-hydroxyphenylpropionyldiamino Hexane

The primary amines tyrosine or 2-hydroxyphenylpropionyl-diaminohexane dissolved in aqueous buffer (35 mM borate buffer, pH 8.5) were added to the p-nitrophenyl carbonate- activated Sepharose (carrying 50–100 mmoles of active group/ g of wet gel).

Reactions were carried out on 3–5 g of gel, in a total volume of 12–15 ml and using a molar ratio of 3:1 between the primary amine and the activated groups of the gel. Suspensions were gently stirred for 150 minutes at room temperature, and the gels were then washed with water, MeOH, EtOAc and then, MeOH and water again. Unreacted active groups in the gel were hydrolyzed by 5 minutes exposure to 0.2M NaOH. Gels were washed again and resuspended in 0.2M KOH (3 g/5 ml) for the final diazotization step.

(ii) Diazotization Reaction.

Anthranilic acid and $NaNO_2$ were dissolved in $H_2O$ (156 mmoles/ml for both) and concentrated HCl (100 ml/ml of water) was added after cooling in an ice bath. The solution was stirred for 5 minutes and then added dropwise to the gel suspended in 0.2M KOH (3 g/5 ml). The reaction was gently stirred for 15 minutes, while the temperature was controlled using an ice bath, and the pH was monitored constantly and adjusted to 8.0–8.5 using diluted KOH. A molar ratio of 1:1 between anthranilic acid and the phenyl residues in the gel was used, assuming that a complete conversion of the activated p-nitrophenyl groups occurred in the previous step of the synthesis. The GEL A obtained was then washed (same procedure as in previous step) and suspended in PBS.

7.4. b Preparation of GEL B

Hydroxyl groups of Sepharose CL-4B were first activated with N,N'-disuccinimidylcarbonate (Wilchek and Miron, 1985), and the activated gel was then coupled to tyramine via the amino group. The HABA derivative was obtained by diazotization of the phenyl residues using anthranilic acid (i) Sepharose-tyramine Tyramine dissolved in PBS (pH 7.4) was added to the N,N'-disuccinimidylcarbonate activated Sepharose (carrying 20–80 mmoles of active groups/g of wet gel). Reactions were carried out on 3–5 g of gel, in a total volume of 12–15 ml and using a molar ratio of 5:1 between the primary amine and the activated groups of the gel. Suspensions were gently stirred overnight at 4° C. Gels were then washed extensively until no more free amine could be detected and unreacted active groups in the gel were hydrolyzed by 5 minutes exposure to 0.2M NaOH. Gels were washed again and resuspended in 0.2M borate buffer (pH 8.5) (3 g/5 ml) for the final diazotization step.

(ii) Diazotization reaction.

Anthranilic acid and $NaNO_2$ were dissolved in $H_2O$ and concentrated 0.2M HCl was added after cooling in a ice bath. The solution was stirred for 5 minutes and then added dropwise to the gel suspended in 0.2M borate buffer (3 g/5 ml). The reaction was gently stirred for 15 minutes, while the temperature was controlled using an ice bath and the pH monitored constantly and adjusted to 8.0–8.5 using diluted KOH. A molar ratio of 1:1 between anthranilic acid and the phenyl residues in the gel was used, assuming that a complete conversion of the activated p-nitrophenyl groups occurred in the previous step of the synthesis. The GEL B obtained was then washed and finally suspended in PBS.

7.5 Affinity Purification of Anti-HABA Polyclonal Antibodies With GEL A and GEL B.

Sepharose GELS A and B were pre-treated with 0.1M TEA pH 11.5 before any further use and re-equilibrated with PBS. Rabbits' antisera diluted 1:1 with PBS or IgG antibodies obtained by $(NH_4)_2SO_4$ precipitation were incubated with the gel for 4 hours at 4° C. Total removal of anti-HABA antibodies from supernatant was verified by dot blot on nitrocellulose paper, using BSA-HABA for dotting. In order to obtain an efficient retention of anti-HABA antibodies, a ratio of 1:1 w/w between serum and gel was used. The gel was then washed extensively with 0.05 M Tris HCl, 0.5M NaCl, pH 7.5. Bound antibodies were finally eluted by basic treatment, using 0.1M TEA, pH 11.5, immediately neutralized and dialyzed against PBS.

7.6 Characterization of Anti-sera and Affinity Purified Anti-HABA Polyclonal Antibodies: Screening for Anti-HABA Antibodies With Different Specificities.

Purity of the affinity purified anti-HABA polyclonal antibodies according to Example 7.5 above was verified by SDS gel electrophoresis. Concentration of an affinity purified anti-HABA antibody solution was determined spectrophotometrically using the average $\epsilon^{\%}_{280\ nm}$ value of 14.5 for IgGs. Specificity of anti-sera and affinity purified antibodies for different epitopes in the HABA molecule was verified by Elisa and UV spectrophotometry.

7.7 ELISA Assay

Ninety-six well microtiter plates (Nunc F96, Maxisorp) were coated by overnight incubation at 4° C. with 50 μl/well of HABAylated avidin solution (10 μg/ml in 0.05 M Na carbonate, pH 9.5). Plates were washed three times with PBS/Tween 0.05% (PBS/T) and blocked by adding 200 μl of PBS/T containing 3% BSA or 0.1% of gelatine. After 2 hours incubation at 37° C., plates were washed three times with PBS/T.

Serial dilutions of antisera or affinity purified anti-HABA antibodies (50 μl) were then incubated for 2h at 37° C. When HABAylated avidin was used for the coating, the experiment was run in duplicate and the antibodies were incubated with and without biotin in the diluting buffer. Plates were washed 3 times with PBS/T and incubated for 2 hours at 37° C. with 50 μl/well of a solution containing HRP-conjugated anti-rabbit antibodies (diluted 1:2,500). After extensive washing with PBS/T, 100 μl of o-phenylenediamine solution were added, the reaction stopped using 1M $H_2SO_4$ and the OD at 490 nm was measured after 5 minutes.

Figure 3:
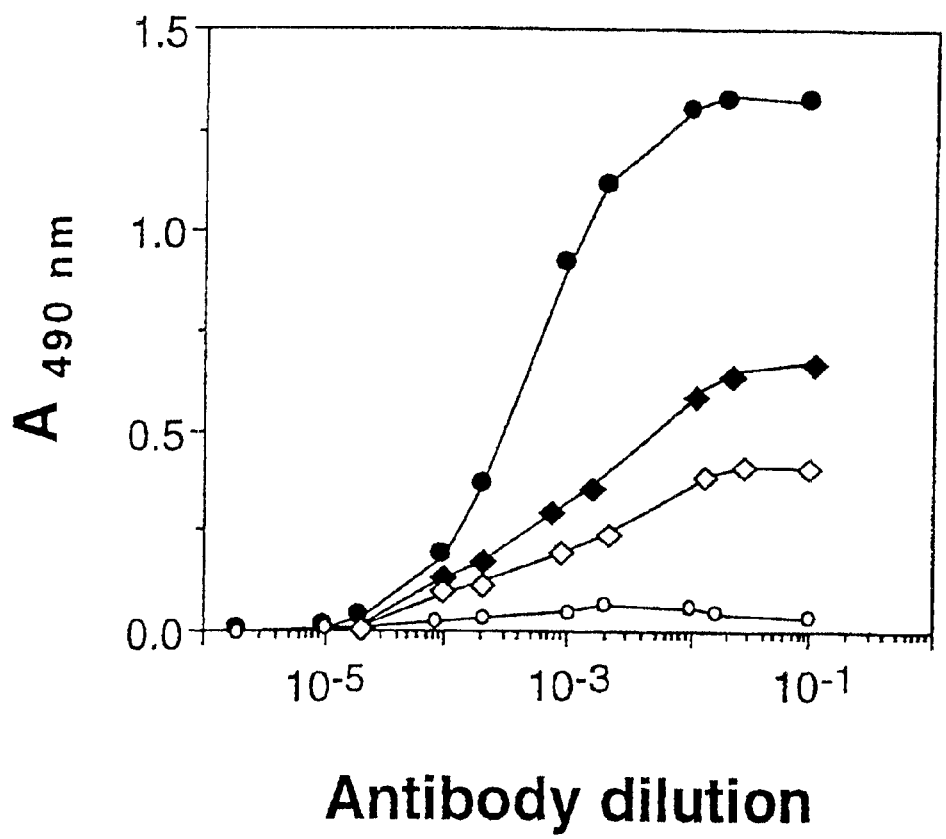
FIG. 3 shows the results of ELISA assay using the polyclonal affinity-purified anti-HABA antibody. Plates were coated with HABAylated avidin, the desired dilutions of antibodies were applied with biotin (◆ Antibody purified on column A, ● Antibody purified on column B) or without biotin (◇ Antibody purified on column A, 0 Antibody purified on column B) and the plates were assayed using a secondary antibody-enzyme conjugate.

Absence of cross reactivity against the anthranilic part of the HABA molecule was verified running a control ELISA assay with BSA-anthranilic acid in the first coating. As shown in FIG. 3, anti-HABA antibodies purified on GEL A were able to recognize HABA as part of the HABAylated avidin in the absence (◊) as well as in the presence of biotin (♦). However, in the absence of biotin, the anti-HABA antibody purified on GEL B failed to recognize the HABA buried in the binding site. Upon addition of biotin, however, the HABA moiety was expelled and strong binding of the anti-HABA antibody was detected (●). This effect clearly depends on the procedure used for purification of the anti-HABA antibodies.

7.8 Spectrophotometry

UV spectra of HABA (compound 0) in PBS was recorded in the presence of the anti-HABA antibodies affinity purified in both GELs A and B. The results indicate that:

Antibodies purified with GEL A (A-anti-HABAs) recognize the HABA moiety when it is either in the azo or the quinone conformation.

Antibodies purified with GEL B (B-anti-HABAs) can bind to the HABA moiety only when it is in the azo conformation whereas they fail to recognize it in the quinone conformation. In this case, recognition of the HABAylated avidin occurs only after biotin expels HABA from the binding pocket.

Example 8

Single-layer Protein System

To prove this principle, HABA was coupled covalently to the binding site of avidin using an appropriate spacer arm. The introduction of biotin or biotinylated compounds served to expel the HABA moiety from the binding site, thereby rendering it available for s further interaction with other binding molecules, e.g., unmodified avidin, anti-HABA antibodies or biotinylated anti-HABA antibodies (FIG. 1). This self-contained system can be used to generate growing cascades of interactions and layers.

As a second HABA-binding molecule, anti-HABA polyclonal antibodies affinity purified on GEL B were used to selectively built a single layer system that is dependent on the addition of biotin as a trigger (FIG. 3), showing that the HABA moiety is indeed buried in the avidin binding site and is not available for further interaction before its displacement by biotin.

Example 9

Multilayer Protein System

Figure 4:
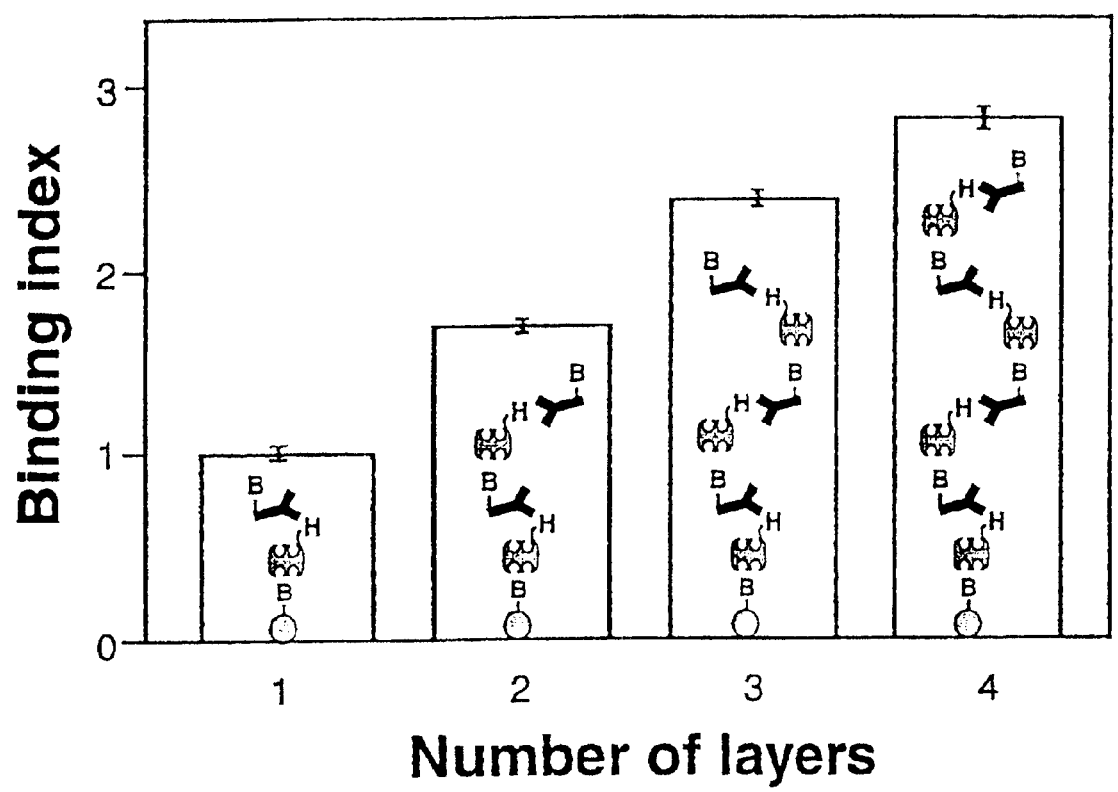
FIG. 4 illustrates an artificial cascade formed by layers generated by consecutive addition of HABAylated avidin and biotinylated antibodies. ELISA plates were coated with biotinylated-BSA (β) to which HABAylated avidin (other symbols are as in FIG. 1) A and biotinylated anti-HABA antibody was added. The cycle was continued several times. Formation of the layers was detected using a secondary antibody-enzyme conjugate. The signal of the first layer was set as binding index=1.

To prove that this system meets the requirements of a signal transduction cascade and the assemblage of protein multilayers (Muller et al, 1993), biotin-saturated HABAylated avidin was incubated with biotinylated anti-HABA antibodies, followed by additional cycles of HABAylated avidin and biotinylated anti-HABA antibodies. A stepwise increase in absorbance could be detected after the formation of each layer (FIG. 4). The assemblage of multilayers could be initiated using HABAylated avidin and either biotin or biotinylated macromolecules. In either case, the addition of biotin was crucial to expel the HABA from the binding site, thus enabling subsequent interaction with the anti-HABA antibodies.

Since avidin has 4 binding sites, if limited amounts of biotin are added to displace only one or two HABA molecules, the system can be triggered vectorially in different dimensions.

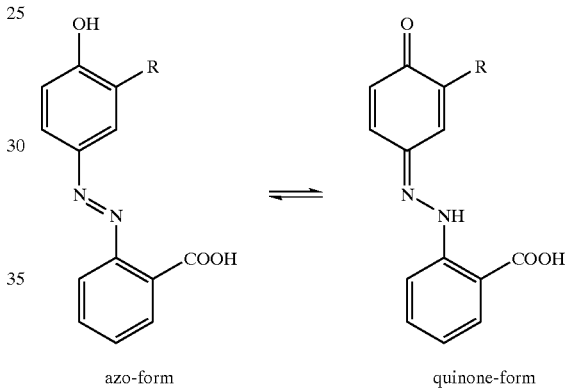

azo-form           quinone-form

Appendix B: STRUCTURES OF COMPOUNDS 1–11

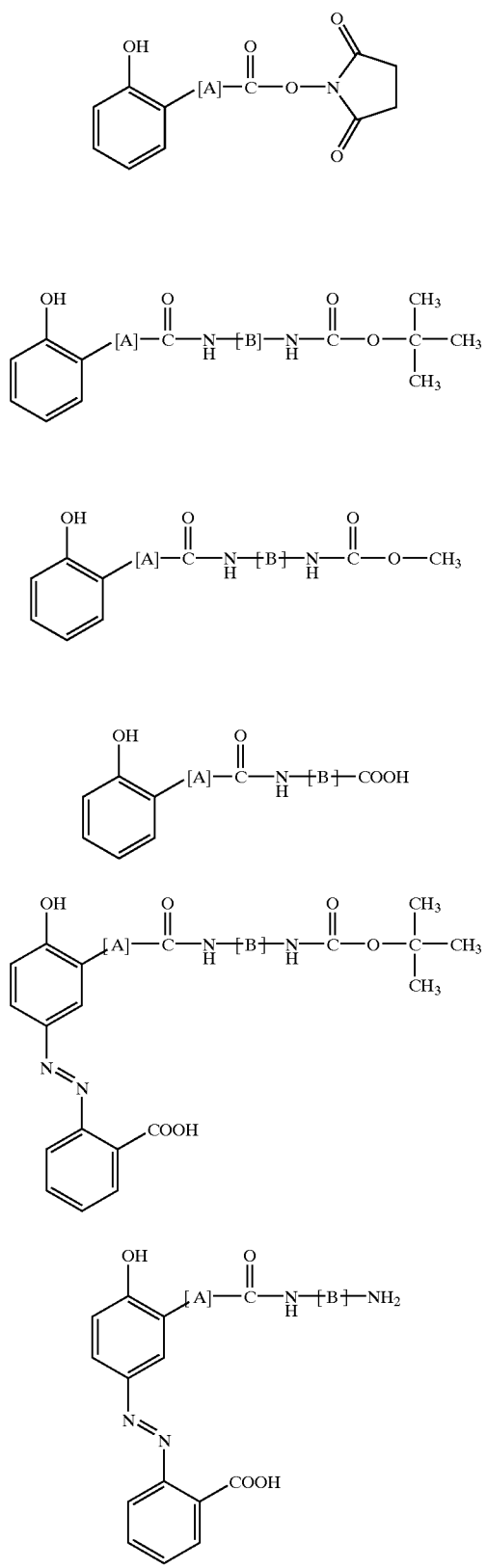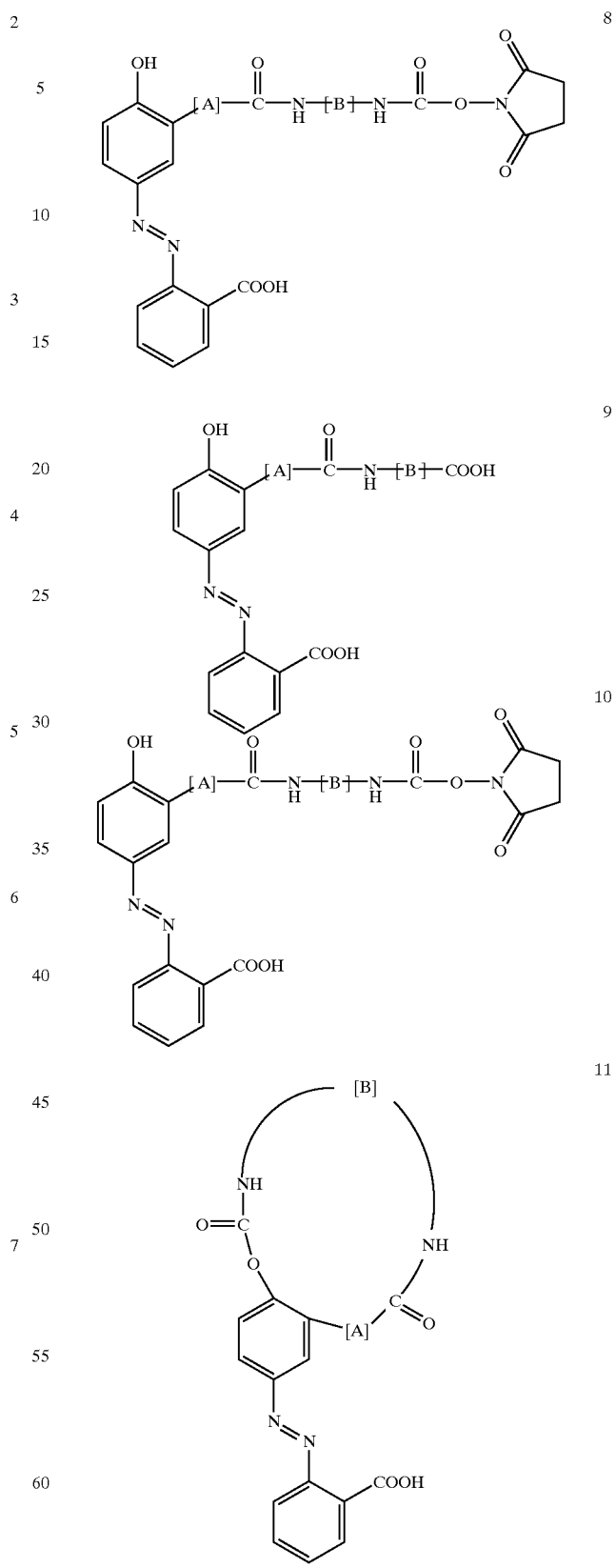

Scheme 1
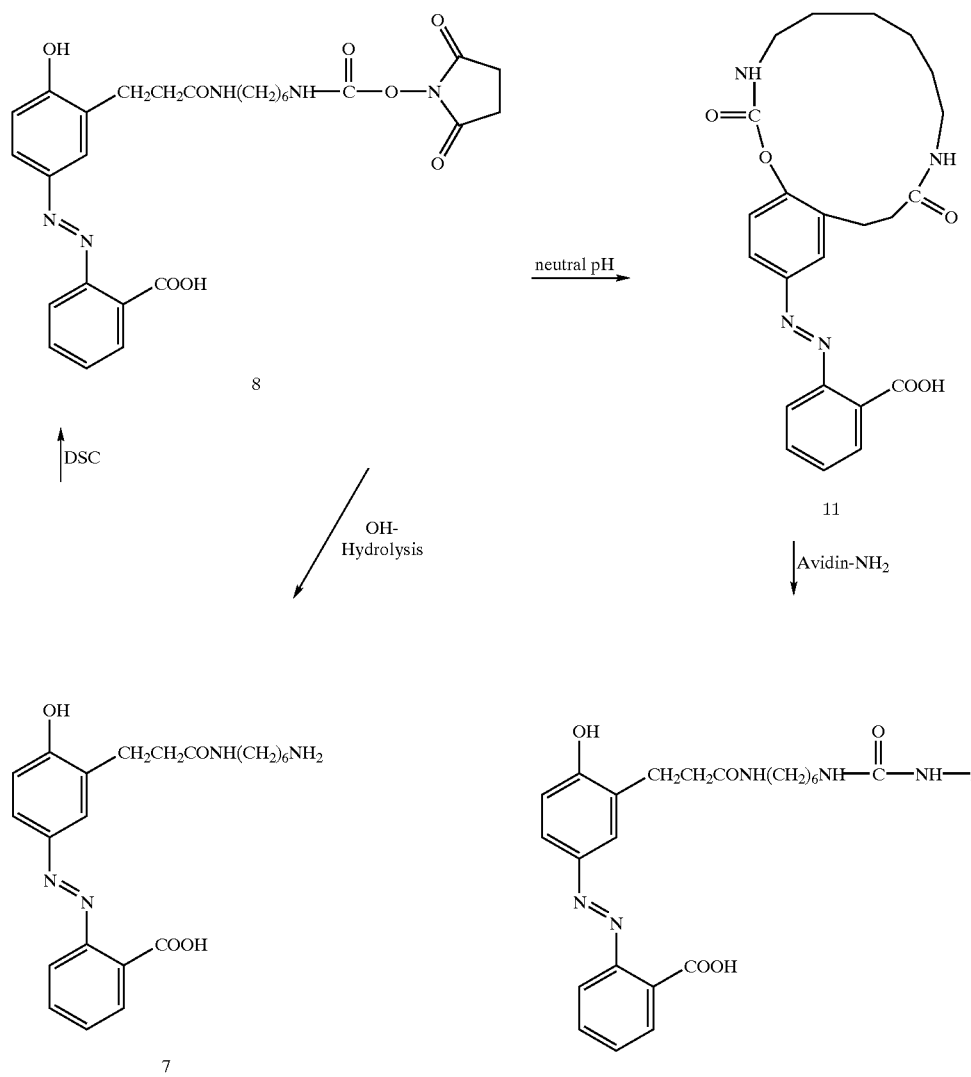
Scheme 2
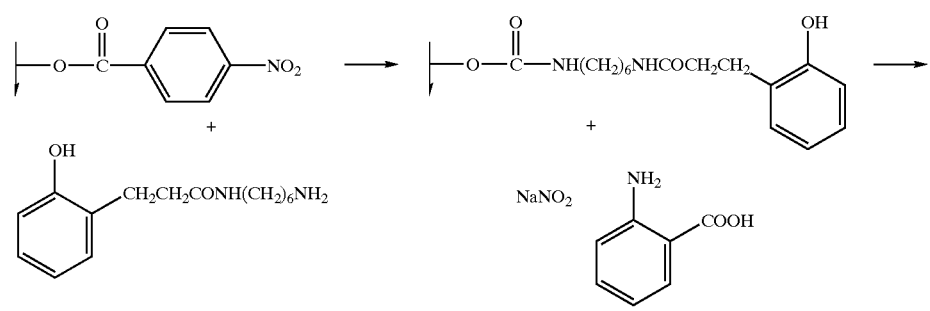

GEL B

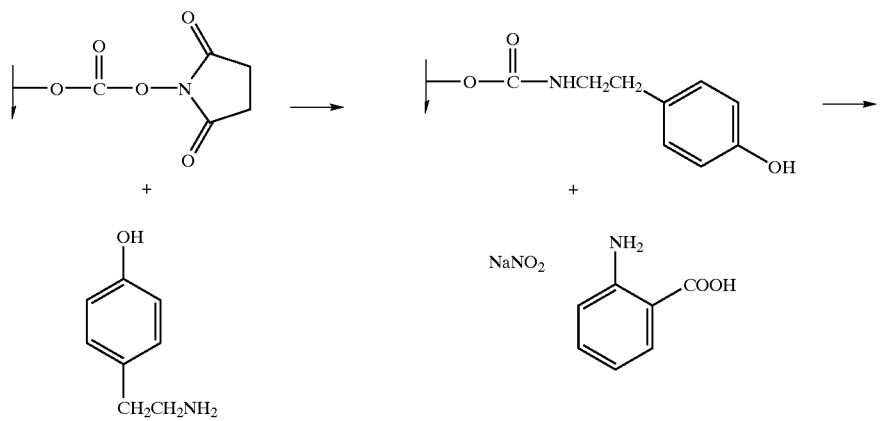

-continued

References

Argarana, C. E.; Kuntz, I. D.; Birken, S.; Axel, R.; Cantor, C. R. (1986), *Nucl. Acids Res.* 14, 1871.

Bannwarth, W. and Knorr, R. (1991), *Tetrahedron Lett.* 32, 1157.

Bayer, E. A., De Meester, F. E., Kulik, T., Wilchek, M. (1995), *Appl. Biochem. Biotechnol.* 53, 1.

Bayer, E. A.; Ben-Hur, H.; Wilchek, M. (1990), *Methods Enzymol.* 184, 80.

Bayer, E. A.; Wilchek, M. (1 990), *Methods Enzymol.* 184, 138.

Bayer, E. A.; Wilchek, M. (1992), *Methods in Molec. Biology* 10, 137.

Chandra, G. and Gray, G. (1990), *Methods Enzymol.* 184, 70.

Garman A., Non-Radioactive Labeling, Academic Press, 1997.

Green, N. M. (1965), *Biochem. J.* 94, 23C–24C.

Green, N. M. (1990), *Methods Enzymol.* 184, 51.

Hiller, Y.; Bayer, E. A.; Wilchek, M. (1990), *Methods Enzymol.* 184, 68.

Müller, W.; Ringsdorf, H.; Rump, E.; Wildburg, G.; Zhang, X.; Angermaier, A.; Knoll, W.; Liley, M.; Spinke J. (1993), *Science* 262, 1706.

Vetter S., Bayer E. A. and Wilchek M. (1994), Avidin can be forced to adopt catalytic activity, *J. Am. Chem. Soc.* 116, 9369.

Wichek, M., Miron T., Kohn J. (1984), Affinity Chromatography, *Meth. Enzymol* 104, 3.

Wilchek, M. and Bayer, E. A. (1990), *Methods Enzymol.* 184, 5.

Wilchek, M. and Miron, T. (1985), *Applied Biochem. Biotechnol.* 11, 191.

What is claimed is:

1. A covalent conjugate of a 4'-hydroxyazobenzene-2-carboxylic acid derivative (hereinafter HABA) and an avidin-type molecule, said conjugate being referred herein as "HABAylated avidin" and having the formula:

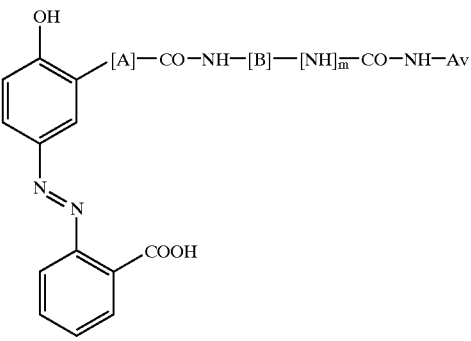

wherein

A is $(CH_2)_n$ or $-CH=CH-$, wherein n is an integer from 0–10;

B is $(CH_2)_n$ wherein n is an integer from 2 to 10;

m is zero or 1; and

Av is the residue of an avidin-type molecule selected from the group consisting of native egg-white avidin, recombinant avidin, deglycosylated avidins, bacterial streptavidin, recombinant streptavidin, and truncated streptavidin.

2. The HABAylated avidin according to claim 1, wherein the benzene ring carrying the OH group is in the quinone configuration and said HABAylated avidin has a red color.

3. The HABAylated avidin according to claim 1, wherein A is $-CH_2-CH_2$ or $-CH=CH-$ and B is $(CH_2)_5$ or $(CH_2)_6$.

4. The HABAylated avidin according to claim 2, wherein A is $-CH_2-CH_2$, m is 1, B is $(CH_2)_6$ and Av is egg-white avidin.

5. A method for the preparation of a HABAylated avidin according to claim 1 wherein m is zero, which comprises reaction of an avidin-type molecule with a succinimidyl ester of a HABA derivative of the formula I:

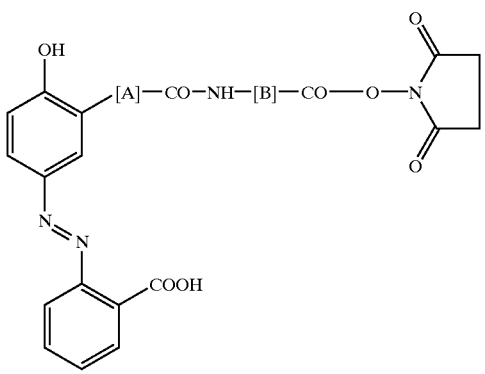

I wherein A is $(CH_2)_n$ or —CH=CH—, wherein n is an integer from 0–10; and B is $(CH_2)n$ wherein n is an integer from 2 to 10.

6. A method for the preparation of a HABAylated avidin according to claim 1 wherein m is 1, which comprises reaction of an avidin-type molecule with a succinimidyl carbamate of a HABA derivative or a cyclic HABA derivative of the formulas II and III, respectively:

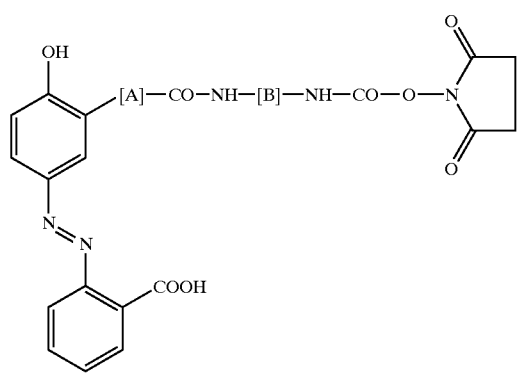

II

III

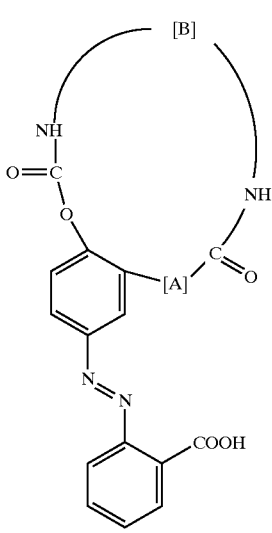

wherein A is $(CH_2)_n$ or —CH=CH—, wherein n is an integer from 0–10; and B is $(CH_2)_n$ wherein n is an integer from 2 to 10.

7. A cyclic HABA derivative of the formula III:

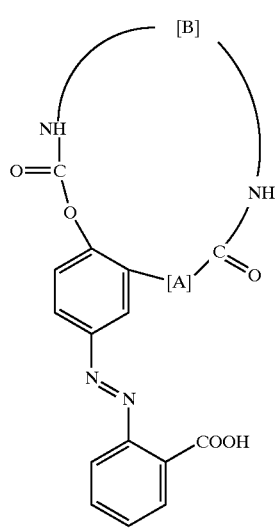

III wherein A is $(CH_2)_n$ or —CH=CH—, wherein n is an integer from 0–10; and B is $(CH_2)_n$ wherein n is an integer from 2 to 10.

8. The cyclic HABA derivative of claim 7 wherein A is $(CH_2)_n$, n is 2 and B is $(CH_2)_6$.

9. A HABAylated avidin-type molecule according to claim 1, attached to a solid support.

10. A HABAylated avidin-type molecule according to claim 9, wherein the solid support is a resin, a microtiter plate, glass beads or magnetic beads.

11. The HABAylated avidin-type molecule according to claim 10, wherein the solid support is a resin.

12. The HABAylated avidin-type molecule according to claim 11, wherein the resin is Sepharose.

13. A column for the immobilization of a biotinylated ligand containing a HABAylated avidin-type molecule of claim 1 attached to a resin.

14. A column according to claim 13, wherein said HABAylated avidin-type molecule is HABAylated native egg-white avidin and said resin is Sepharose.

15. A column according to claim 13, wherein said HABAylated avidin-type molecule is HABAylated deglycosylated avidin and said resin is Sepharose.

* * * * *